(12) United States Patent
Denolly

(10) Patent No.: US 7,704,236 B2
(45) Date of Patent: Apr. 27, 2010

(54) DISTRIBUTION DEVICE FOR A SUPPLY NETWORK FOR SUPPLY OF MEDICAL FLUIDS TO A PATIENT

(75) Inventor: Pascal Denolly, Jardin (FR)

(73) Assignee: SEDAT, Irigny (FR)

( * ) Notice: Subject to any disclaimer, the term of this patent is extended or adjusted under 35 U.S.C. 154(b) by 146 days.

(21) Appl. No.: 10/539,577

(22) PCT Filed: Dec. 19, 2003

(86) PCT No.: PCT/FR03/03854

§ 371 (c)(1),
(2), (4) Date: Dec. 14, 2005

(87) PCT Pub. No.: WO2004/058331

PCT Pub. Date: Jul. 15, 2004

(65) Prior Publication Data

US 2006/0161113 A1    Jul. 20, 2006

(30) Foreign Application Priority Data

Dec. 20, 2002    (FR)    .................................. 02 16432

(51) Int. Cl.
*A61M 5/00*    (2006.01)
(52) U.S. Cl. ........................... 604/191; 604/13; 604/30; 604/33; 604/35; 604/66; 604/67; 604/151
(58) Field of Classification Search ................ 604/131, 604/19, 27, 30, 31, 32, 33, 35, 48, 66, 67, 604/93.01, 151, 152, 187, 247, 258, 83, 191; 600/431, 432, 433; 417/63, 440, 571
See application file for complete search history.

(56) References Cited

U.S. PATENT DOCUMENTS

| | | | |
|---|---|---|---|
| 3,859,985 A | | 1/1975 | Eckart |
| 4,296,785 A | * | 10/1981 | Vitello et al. ................ 141/105 |
| 4,608,996 A | * | 9/1986 | Brown ......................... 600/579 |
| 4,645,496 A | | 2/1987 | Oscarsson |
| 4,838,866 A | * | 6/1989 | Marshall, Sr. ................ 604/152 |
| 5,423,751 A | * | 6/1995 | Harrison et al. ................ 604/83 |
| 5,562,611 A | * | 10/1996 | Transue ........................ 604/26 |
| 6,638,258 B2 | * | 10/2003 | Schwartz et al. ............. 604/247 |

(Continued)

FOREIGN PATENT DOCUMENTS

EP    1 074 221    2/2001

*Primary Examiner*—Nicholas D Lucchesi
*Assistant Examiner*—Quynh-Nhu H Vu
(74) *Attorney, Agent, or Firm*—Sughrue Mion, PLLC

(57) ABSTRACT

This distribution device comprises a syringe body (30), a distributor (32), a feed tube (56) for a first active medical fluid opening into the syringe body (30), a tube (60) for the injection of this active fluid connected to a distal extremity (46) of the syringe body (30), a pressurized tube (64) designed to be connected to a patient through a pressurized line (12) and a tube (66) for the measurement of venous or arterial pressure. The pressurized, injection and measurement tubes open into a chamber (62) bounded within the body (32B) of the distributor (32). The device (2) comprises a flush tube (68) which is at least partly bounded by the body (32B) of the distributor (32), which opens into the chamber (62) and is fitted with a valve (70, 80) which can be operated manually.

11 Claims, 6 Drawing Sheets

U.S. PATENT DOCUMENTS

| | | | |
|---|---|---|---|
| 6,650,929 B1 * | 11/2003 | Nemoto et al. | 600/431 |
| 6,699,232 B2 * | 3/2004 | Hart et al. | 604/523 |
| 6,866,654 B2 * | 3/2005 | Callan et al. | 604/247 |
| 6,953,450 B2 * | 10/2005 | Baldwin et al. | 604/248 |
| 2002/0123737 A1 * | 9/2002 | Hart et al. | 604/523 |
| 2002/0151854 A1 | 10/2002 | Duchon et al. | |
| 2004/0082904 A1 * | 4/2004 | Houde et al. | 604/33 |

* cited by examiner

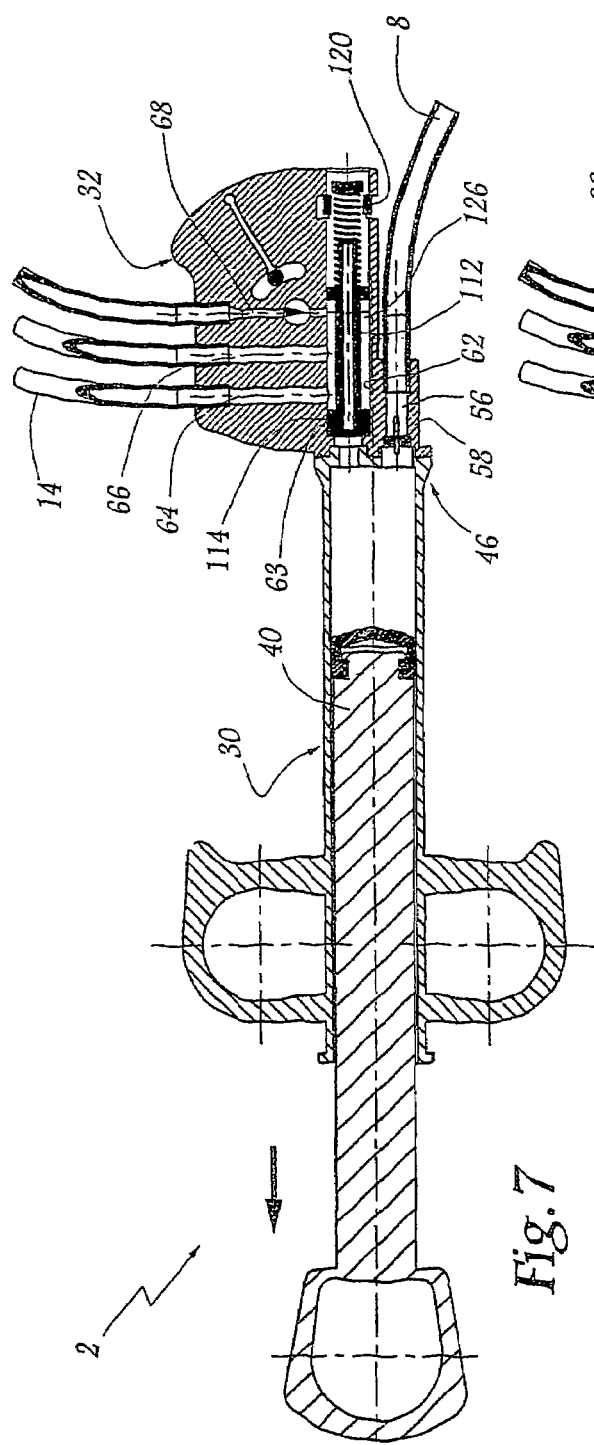
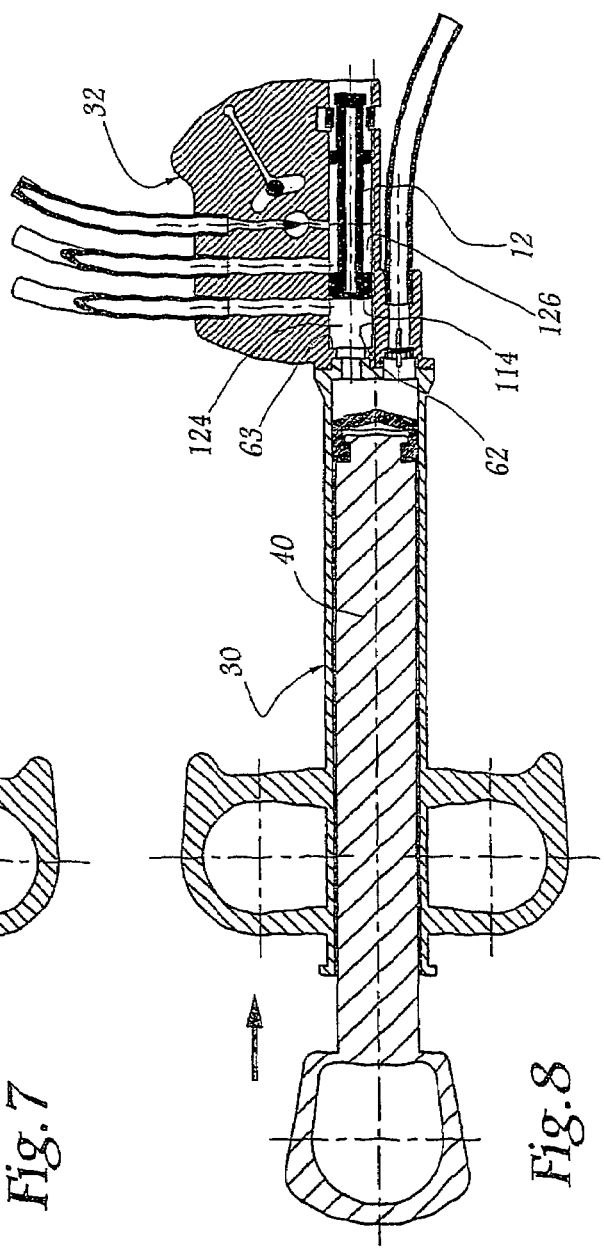
Fig. 7
Fig. 8

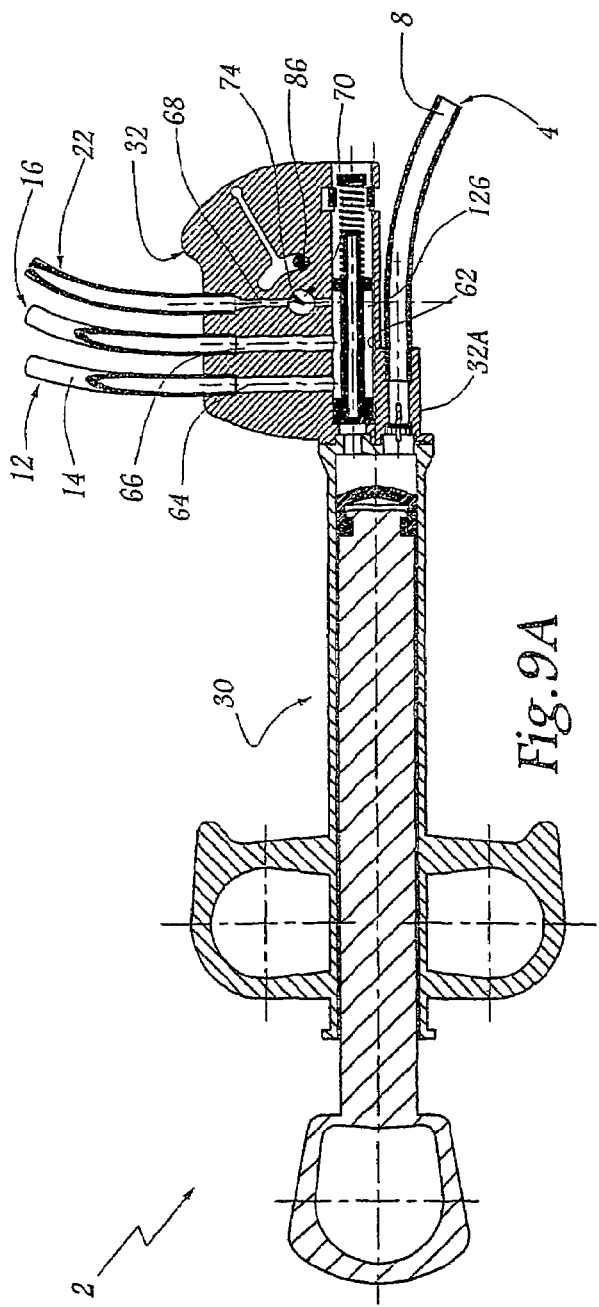
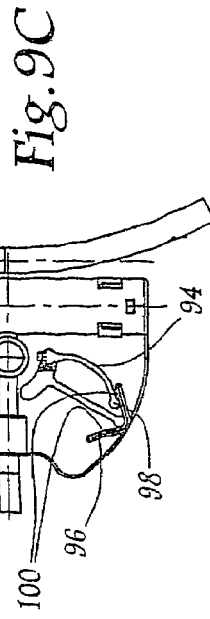
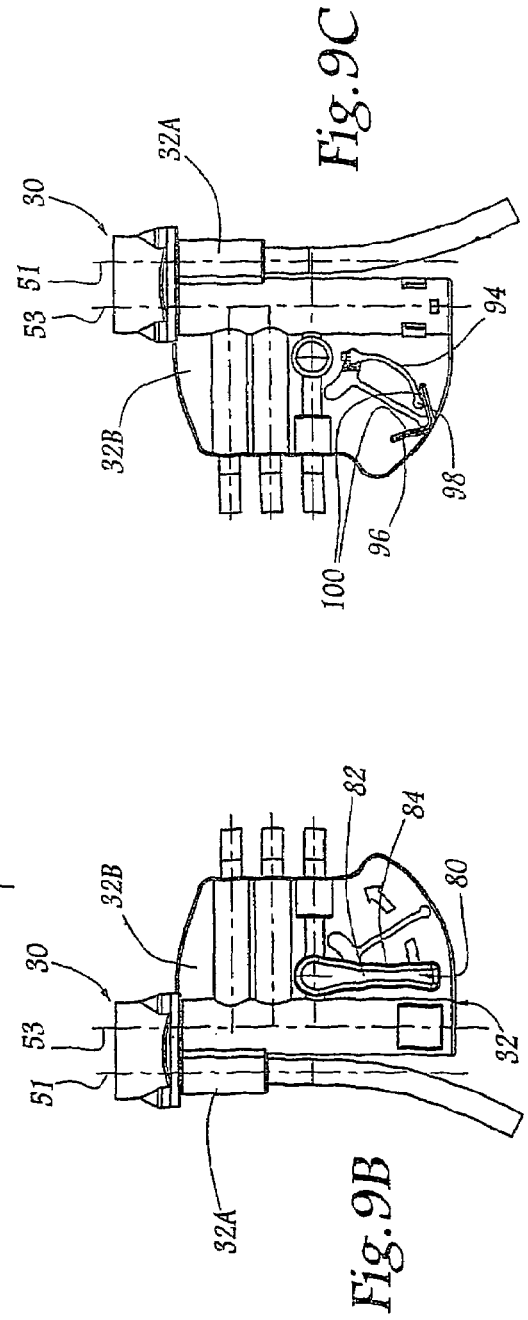

DISTRIBUTION DEVICE FOR A SUPPLY NETWORK FOR SUPPLY OF MEDICAL FLUIDS TO A PATIENT

BACKGROUND OF THE INVENTION

This invention relates to a distribution device for a system for the delivery of medical fluids to a patient. It also relates to a kit for injection of a contrast product into the human body.

This type of distribution device is in particular used in the course of diagnostic and therapeutic procedures in interventional radiology. In fact in this particular context doctors inject a contrast product into the patient's arteries or veins, checking the pressure of the artery into which the product is introduced from time to time. For this purpose the doctor creates a system for delivery of the contrast fluid to the patient using a set of flexible tubes connected to different tubes or channels in the distribution device.

In the course of these interventional radiology procedures it is frequently necessary to clean at least part of the distribution device, in particular the tube and the catheter attached thereto which delivers the contrast product to the patient, because of that fluid's tendency to set and deposit on the walls of the tube and the catheter after being immobile for some time. For this purpose the distribution devices incorporate a line known as a "rinsing" or "flush" line in which a saline solution or serum which is designed to carry off the contrast product previously used circulates under pressure.

A first type of distribution device appropriate for such an application comprises an assembly of at least two three-way taps mounted in series. Each of the taps comprises a separate manual control member.

In order that the contrast fluid may be injected, one of the channels of the first tap is connected by a line to the patient fitted with a catheter. The remaining channel of the same tap is connected to a pressure sensor connected to the flush line. A first channel of the second tap is connected to a reservoir of contrast product. A suction and injection syringe is connected to the second channel of the second tap.

The two taps make it possible to define two connection configurations between the various components of the system, these two configurations being used successively and repeatedly. In a first configuration the syringe is connected to the reservoir of contrast product while the pressure sensor is connected to the patient. In this first configuration contrast fluid may be drawn off by the doctor using the syringe and the flush liquid circulates to the patient. In the second configuration the bottle containing the contrast fluid, as well as the pressure sensor and the flush line, are isolated from the system, while the syringe is placed in communication with the patient. In this second configuration the doctor can inject contrast fluid into the patient. It will be understood that when using a distribution device comprising an assembly incorporating two three-way taps mounted in series the doctor will have to operate the two taps whenever he wishes to change the system between the two useful configurations. This manipulation is a source of error, in particular because the doctor may forget to operate one of the two taps. In addition to this the doctor must use both hands, one to hold the body of the taps and the other to operate the two controls for the taps in succession, rendering the operation relatively long.

A second type of distribution device suitable for the aforesaid application comprises a distributor incorporating a body which bounds internally a fluid circulation chamber into which there open an injection tube for the contrast medium, a pressure measurement tube connected to an arterial or venous pressure measurement line and a pressurised tube, sometimes called the "patient tube" connected to a line provided with a catheter to deliver the contrast fluid to the patient's artery or vein. Using a movable slide located within the chamber the doctor selectively connects the tube under pressure with either the injection tube or the pressure measuring tube. So that injection may be performed under sufficient pressure, the injection tube is connected to the distal extremity of a syringe body into which there opens a contrast fluid feed tube connected to a reservoir for that product. In order that at least the tube under pressure and the line connected thereto may be flushed, the flush line is connected to the pressure measuring tube and is provided with a closing member of the non-return valve type so that the flush solution can run through the tube under pressure connected to the patient when that tube is connected to the pressure tube via the slide chamber, by using a driving pump located in the flush line.

It will be understood that with such a distribution device the doctor must at the same time check that the movable slide within the chamber is in the correct position and that the pump driving the saline solution is correctly operating each time it is desired to flush the device.

Although this manipulation is simpler than that for a device having several taps, it remains difficult, in particular because the doctor may incorrectly adjust the flush fluid driving pump and thus disturb movements of the slide within the connecting chamber of the distributor. In addition to this manipulation of the pump is relatively time-consuming, particularly as it is not necessarily located close to the doctor, whose hands are holding the distribution device which has to be flushed.

SUMMARY OF THE INVENTION

The object of the invention is to provide a distribution device having a distributor as described above, in which flushing is simplified for the doctor, thus reducing risks of error and loss of time.

For this purpose the invention relates to a distribution device for a system for the delivery of medical fluids to a patient, of the type comprising:
  a syringe body,
  a distributor comprising a body within which there is bounded a chamber for fluid circulation,
  a feed tube for an active medical fluid, opening into the syringe body and designed to be connected to a reservoir for the said active fluid,
  a tube for the injection of this active fluid connected to the distal extremity of the syringe body and opening into the distributor chamber,
  a tube under pressure which is designed to be connected to the patient through a pressurised line in the system and opening into the distributor chamber,
  a pressure measurement tube designed to be connected to a pressure measurement line of the system and opening into the distributor chamber, this distributor being designed to connect the pressurised tube with only one of the injection and pressure measurement tubes via the said chamber, and
  a flush tube designed to be connected to a reservoir for a medical flush fluid and designed to be connected to at least the pressurised tube, in which the flush tube is bounded, at least partly, by the body of the distributor, opens into the chamber and is provided with a manually operable valve which can be moved between a position which at least partly closes the flush tube and a position in which the flush tube is in free communication with the chamber.

According to other features of this device, taken in isolation or in all technically possible combinations:
the flush tube valve is mounted on the distributor body,
the valve is rotatably mounted about an axis orientated transversely to the flush tube,
the flush tube valve comprises a plug for the tube and a manual control lever, the plug and the lever being connected mechanically to each other and moving in relation to the distributor body,
the plug comprises a sector of a cylinder,
the device comprises means for resiliently turning the valve to its closed position,
the resilient means comprise a flexible blade bearing against the body of the distributor and mechanically connected to the flush tube valve,
the distributor body is integral with the body of the syringe in a leaktight manner,
the feed tube for the first active medical fluid is bounded by the distributor,
the feed and injection tubes for the active medical fluid extend in substantially parallel directions, and
within the fluid connection chamber the distributor comprises a slide which is capable of movement in relation to the body of the distributor and a resilient member placed between the said slide and a fixed part of the distributor.

The invention also relates to a kit for the injection of a contrast product into the human body, characterised in that it comprises:
a distribution device as defined above,
a contrast product feed line comprising a flexible conduit equipped with a drip chamber and designed to be connected at one extremity to a reservoir for contrast fluid and at its other extremity to the feed tube of the distribution device,
a pressurised line comprising at one extremity a coronarography catheter designed to be inserted into the patient's body and designed to be connected at its other extremity to the pressurised tube of the distribution device,
a pressure measurement line comprising a conduit fitted with a pressure sensor and designed to be connected to the pressure measurement tube of the distribution device, and
a flush line comprising a flexible conduit fitted with a drip chamber and designed to be connected at one extremity to a reservoir for the flush solution and its other extremity to the flush tube of the distribution device.

The invention will be better understood from a reading of the following description, provided purely by way of example and with reference to the drawings, in which:

DETAILED DESCRIPTION OF THE INVENTION

Figure 1:
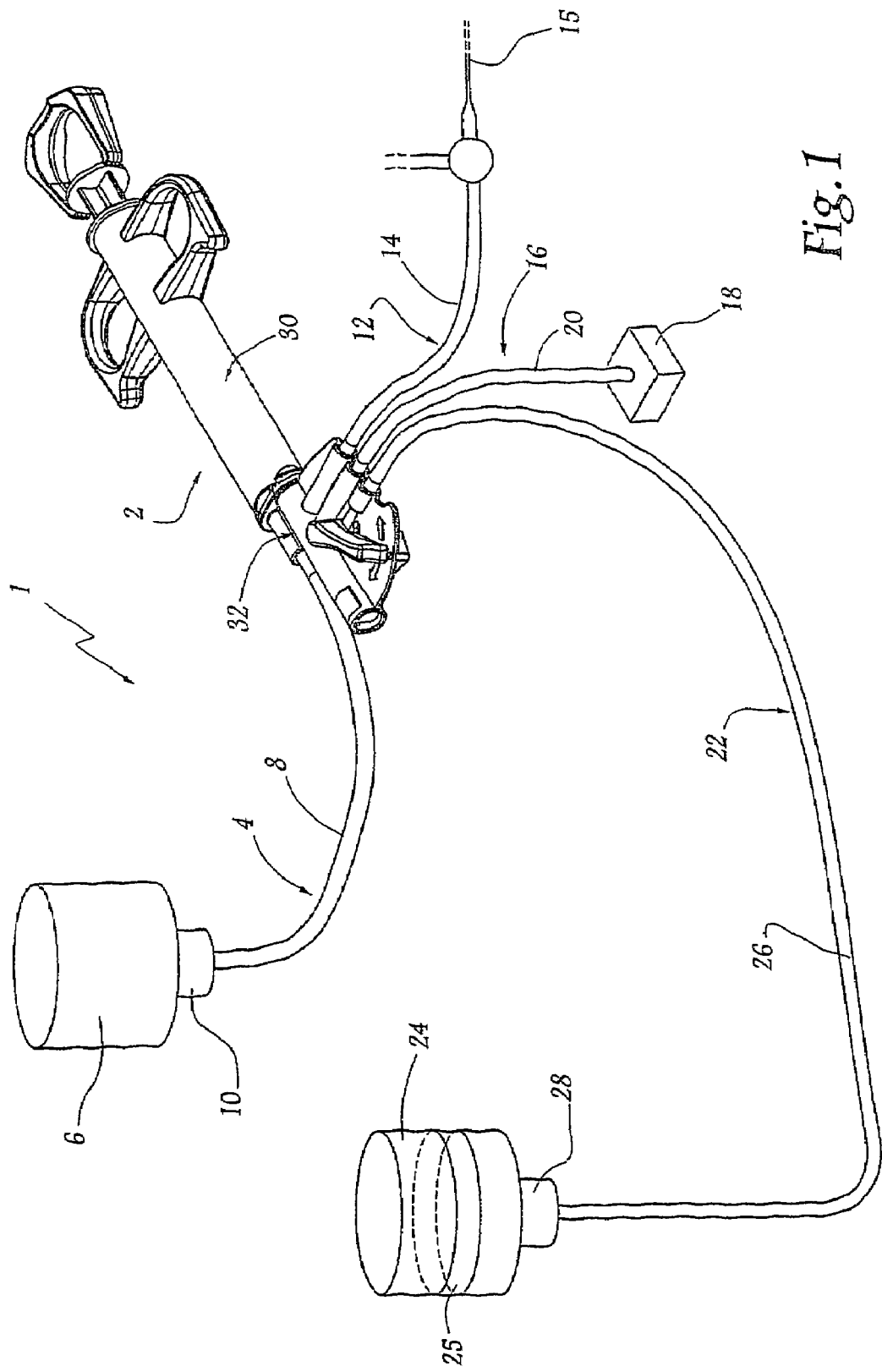
FIG. 1 is a partial perspective view of a system for delivering fluids comprising a distribution device according to the invention.
Figure 2:
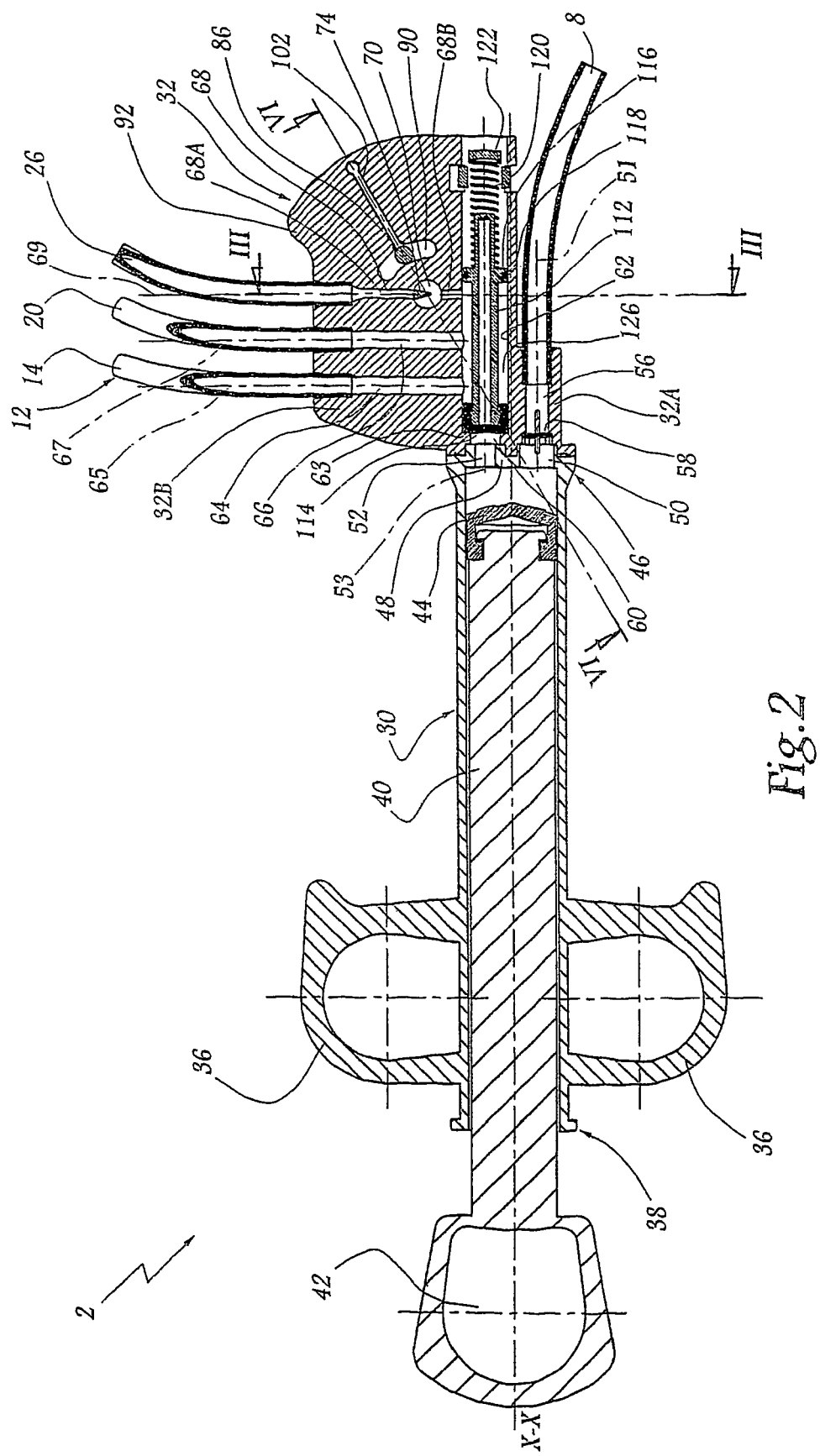
FIG. 2 is a view of the distribution device of the system in FIG. 1 in longitudinal cross-section.
Figure 3:
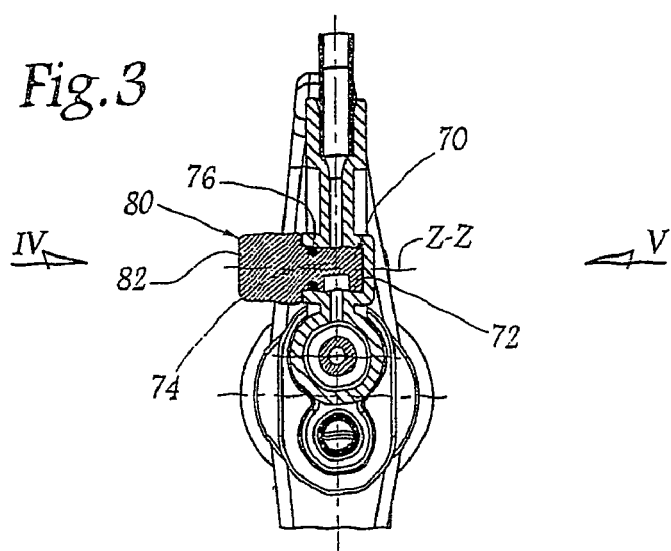
FIG. 3 is a view in cross-section along the plane III-III indicated in FIG. 2, FIGS. 4 and 5 are lateral views part of the extremity of the device in FIG. 2 shown along the arrows IV and V indicated in FIG. 3 respectively.
Figure 4:
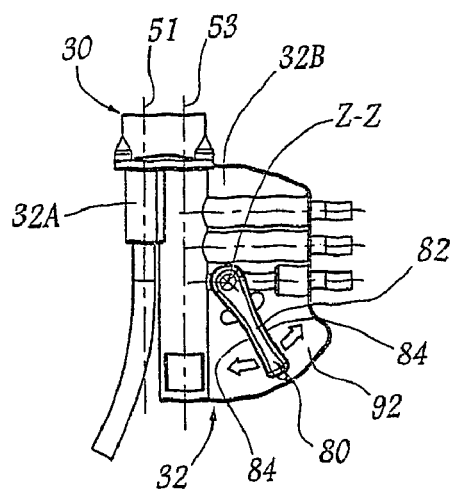

FIG. 1 shows a system 1 for the delivery of medical fluids used in interventional radiology procedures. System 1 comprises:
a device 2 for the distribution of fluids,
a line 4 feeding a contrast fluid comprising a reservoir 6 for that fluid and a flexible conduit 8 connecting the reservoir to distribution device 2; conduit 8 is provided with a drip chamber 10 incorporating a filter and an air intake,
an outlet line 12 for the pressurised contrast fluid comprising a flexible conduit 14 of which one extremity is connected to a device 2 and of which the other extremity is provided with a three-way tap; one of these lines is fitted with a luer connection, extended by a coronarography catheter 15 which when in operation is inserted into the patient's artery or vein,
an artery or vein pressure measurement line 16 comprising a pressure sensor 18 and a flexible conduit 20 connecting that sensor to device 2, and
a flush line 22 comprising a flexible reservoir 24 for the flush solution, for example a saline solution, and a conduit 26 connecting this reservoir 24 to device 2; an inflatable cuff 25 surrounds reservoir 24 in such a way that by increasing the pressure obtaining within that cuff, using for example an inflating bulb, the reservoir is kept at a sufficient pressure to drive the flush solution along the line 22; conduit 26 is provided with a drip chamber 28.

Distribution device 2, which is illustrated in greater detail in FIGS. 2 to 6, essentially incorporates a syringe body 30 and a distributor 32.

Syringe body 30 takes the form of a hollow cylinder having an axis X-X with externally a pair of rigid handles 36 used to grasp device 2. Cylindrical body 30 comprises a proximal extremity 38 within which there is fitted a piston 40 which can move in translational movement along axis X-X. The proximal extremity of piston 40 has an opening 42 for manual operation of the piston and its distal extremity is fitted with a sliding head 44 which maintains a leaktight contact with the inner surface of the syringe body.

Body 30 comprises a distal extremity 46 forming a plate 48 closing off the body, pierced by two cylindrical orifices 50, 52 having axes 51, 53 respectively, parallel to the X-X axis and located on either side of this X-X axis.

Distributor 32 is constructed of a rigid material, for example of moulded plastics, and is rendered sealingly integral with the distal extremity 46 of syringe body 30, in particular through ultrasound welding to closing plate 48. Several cylindrical tubular orifices are formed with distributor 32.

A first tube 56 is formed coaxially with orifice 50, in a first body 32A of distributor 32 which has an essentially cylindrical external shape. At its distal extremity this tube is arranged to be connected to conduit 8 of line 4 feeding the contrast fluid. At its proximal extremity tube 56 opens into orifice 50 and is fitted with a resiliently deformable silicone valve 58 designed to permit communication between tube 56 and the internal volume of syringe body 30 when the pressure obtaining in that syringe body is less than that obtaining in tube 56.

Distributor 32 comprises a second body 32B which is integral with first body 32A, these two bodies being formed as a single piece. Within this body 32B a second tube 60 is formed coaxially with orifice 52 and thus directly connects the internal volume of syringe body 30 with a cylindrical chamber 62 provided in body 32B, coaxially with tube 60. The diameter of this chamber is larger than that of tube 60 so as to form a shoulder 63.

Tubes 64, 66 and 68, having axes 65, 67 and 69 respectively which are parallel to each other, are formed within body 32B in a direction substantially perpendicular to the X-X axis. Tubes 64, 66 and 68 each open directly into chamber 62 at one of their extremities and at their other extremities are designed to be connected to conduit 14 of exit line 12 for the pressurised contrast fluid and conduit 20 of pressure measurement line 16 and conduit 26 of flush line 22 respectively.

Unlike tubes 64 and 66 which place chamber 62 directly in communication with lines 12 and 16 respectively, tube 68, which has a smaller diameter than tubes 64 and 66 in its ordinary part, comprises two sections 68A, 68B separated by a plug 70. This plug essentially has a cylindrical shape having an axis Z-Z substantially perpendicular to the plane in which the X-X axis and the axis [69] of tube 68 lie. Plug 70 is housed within a matching cylindrical recess 72 formed by distributor 32. The ordinary part of the cylinder forming this plug comprises a sector 74 designed to close off the adjacent extremity of 68A.

Plug 70 moves with respect to distributor 32 in a rotational movement about the Z-Z axis so as to alter the angular position of sector 74 within housing 72 and thus place the two parts 68A and 68B of tube 68 in fluid communication. The mounting for plug 70 is rendered leaktight by housing 72 which is closed at one of its extremities and by an O-ring 76 positioned between the walls of the housing and the plug at the other extremity of housing 72.

In order to control the rotational movement of plug 70, distribution device 2 has a manually operated control lever 80. This lever comprises a body 82 of substantially rectangular shape connected to plug 70 in a fixed way in such a way as to cause the handle to turn about the Z-Z axis in relation to distributor 32. In the device illustrated the plug and the handle are constructed as one piece.

Body 82 of handle 80 comprises two opposite lateral sides which are designed to form surfaces 84 against which fingers may press when manual stress is applied to turn the handle. On the side facing distributor 32, body 82 of this handle is provided with a projecting cylindrical pin 86 inserted into a guide groove 90 formed in a plate 92 of body 32B of distributor 32. This groove extends in an arc of a circle centered on the Z-Z axis, over a predetermined distance so that when pin 86 reaches one end of that groove handle 80 is sufficiently turned about the Z-Z axis to release sector 74 from the extremity of part 68A of tube 68.

Distribution device 2 is also provided with resilient means for returning handle 80 to its closed position in which it places sector 74 angularly substantially along the axis 69 of tube 68 as illustrated in FIGS. 2 to 6. These means comprise a flexible blade 94 mechanically connected to body 82 of handle 80 of one piece with pin 86. This blade extends parallel to the side of body 82 facing plate 92. In the embodiment illustrated, blade 94 is formed of a single piece together with pin 86 and body 82 of the handle.

Figure 5:
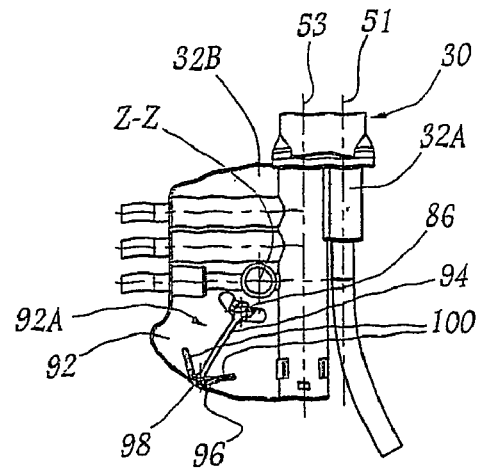

The resilient returning means also comprise an edge 96 projecting from surface 92A of plate 92 opposite handle 80. This edge has a V-shaped cross-section and its tip receives internally the free extremity of blade 94, as illustrated in FIG. 5. More particularly, this free extremity is in the shape of a sphere 98 designed to act together with the facing surfaces 100 of edge 96 so as to constrain the body of blade 94 to deform resiliently in an arc of a circle when handle 80 is turned about the Z-Z axis, by restricting the free movement of this sphere 98 (FIG. 9C).

Figure 6:
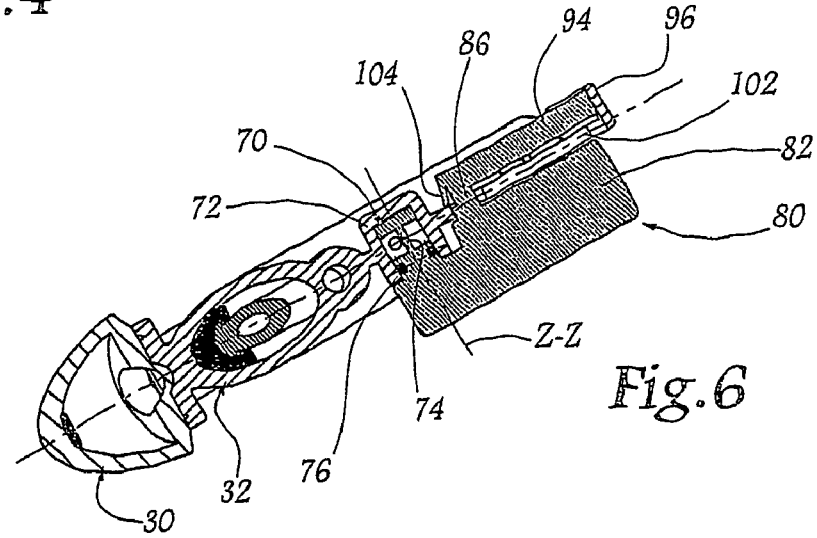
FIG. 6 is view in cross-section along the plane VI-VI indicated in FIG. 2, FIGS. 7, 8 and 9A are views similar to FIG. 2 illustrating three successive stages in use of the device in FIG. 2, FIGS. 9B and 9C are views similar to FIGS. 4 and 5 of the device at the stage illustrated in FIG. 9A.

For the purposes of assembling the assembly comprising plug 70, handle 80 and blade 94 on distributor 32, a groove 102 of a shape matching blade 94 which extends substantially along the bisector of the angle formed by the V of edge 96 is provided in plate 92 and opens into curved groove 90, with the result that this assembly can be fitted into place by causing blade 94 to pass along the side of plate 92 opposite handle 80. As illustrated in FIG. 6, the extremity of the blade integral with pin 86 is provided with a clip 104 retaining the aforesaid assembly on distributor 32, this clip 104 being resiliently deformed when the assembly is fitted in place, bearing against the surface 92A of the plate. In the embodiment illustrated this clip is formed of one piece with 94.

Device 2 also comprises a slide 112 which can move in translation along the axis 53 of chamber 62, equipped at its proximal extremity with a head 114 in leaktight contact with the walls of the chamber and at its distal extremity with an annular edge 116 fitted with a sealing joint 118 for selectively connecting the second 60, third 64, fourth 66 and fifth 68 tubes via chamber 62. Head 114 and edge 116 are axially offset by at least the distance separating tubes 64 and 68.

A compression spring 120 is fitted between edge 116 and a rigid cover 122 integral with body 32B of the distributor, for example by clipping. Slide 112 thus forms a proximal compartment 124, not illustrated in FIGS. 2 to 6, of variable volume according to the position of the slide within the chamber, with the walls of chamber 62, and also a distal compartment 126 of constant volume between head 114 and edge 116.

Delivery system 1 and device 2 which it incorporates is used as follows:

When catheter 15 is inserted into a patient's artery or vein and the set of components in system 1 are suitably connected as in FIG. 1, the doctor starts a first stage of filling syringe body 30 from contrast fluid reservoir 6. For this purpose, as illustrated in FIG. 7, piston 40 is moved in relation to the syringe body in such a way as to create negative pressure in the distal part 46 of the syringe body. The pressure difference between the interior of the syringe body and first tube 56 causes deformation of valve 58 and filling of the distal part of the syringe body with contrast fluid. During this first stage, head 114 of slide 112 is held against shoulder 63 by spring 120 in such a way that the volume of compartment 124 is zero and catheter 14 is placed in communication with pressure sensor 18 through the connection between tube 64 and tube 66 via compartment 126 bounded by chamber 62.

In order to proceed with injection proper of the contrast fluid, the doctor establishes a connection between syringe body 30 and tube 64 in the course of a second stage. In order to do this, as illustrated in FIG. 8, he moves piston 40 in the direction of distributor 32 so as to increase the pressure of the contrast fluid until the latter pushes slide 112 in the same direction, then connecting tubes 60 and 64 via compartment 124. The contrast product then circulates to the patient.

In this second stage pressure sensor 18 is isolated from pressurised tube 64 by the head 114 of slide 112, and contrast fluid reservoir 6 is isolated from syringe body 30 by valve 58 which is not deformed.

Once piston 40 has reached the end of its travel the doctor moves the piston back towards the proximal part of the syringe body. Compression spring 112 then automatically pushes the slide back in the direction of the syringe body so that tubes 64 and 66 are again connected by chamber 62 as in the first stage, enabling the doctor to know the pressure obtaining in pressurised line 12, i.e. the patient's arterial or venous pressure.

After the contrast fluid has been immobile in tube 64 and in pressurised line 12 for some time they need to be flushed in order to prevent the contrast product from setting and/or becoming fixed to the walls of these components, in particular in their parts of small diameter. In order to do this, in a third stage of use illustrated in FIGS. 9A to 9C, the doctor, who is already holding syringe body 30 in one hand, uses his other hand to operate control lever 80 turning it about the Z-Z axis in one direction or the other until it occupies an extreme position in which pin 86 is located in one of the ends of groove 90.

The doctor's turning the handle and holding it in that turned position causes plug 70 to rotate, which provides free passage for the flush solution from reservoir 24 to compartment 126, as illustrated in FIGS. 9A, 9B and 9C. The flush solution then circulates in tubes 64 and 66 via chamber 62, and therefore in lines 12 and 16. The contrast fluid previously used is carried over by the saline solution, and any air bubbles which have been retained along pressure line 16 are evacuated in order to reduce the risk of incorrect pressure measurements.

Once flushing has been carried out, the doctor releases handle 80 which resumes its initial position through acting together with blade 94 and edge 96 which resiliently returns the handle, and thereby replacing plug 70 into the position closing off flush tube 68. Device 2 is then back in its original condition.

The distribution device according to the invention also enables the doctor to easily flush the main part of the device in a short time and without having to operate systems outside the device which the doctor is holding in his hand, such as a separate pump. The fact that distributor 32 is made of one piece with syringe body 30 makes it possible to obtain a compact device, even in the case of a manual injection device as described hitherto. Inasmuch as the flush tube opens directly into chamber 62, without for example any intermediate connection, the formation of bubbles in the system during flushing is considerably reduced.

In a variant which is not illustrated the geometry of the peripheral surface of closing sector 74 of plug 70 is designed in such a way that at least a small flow of flush fluid is maintained regardless of the position of plug 70. In this way, even when handle 80 is not operated by the doctor, a small quantity of flush solution continuously runs into compartment 126 from chamber 62. In this way the magnitude of any back flow of contrast fluid and/or or blood while head 114 of slide 112 moves back against shoulder 63, that is to say at the very end of the injection stage, is restricted.

Figure 10:
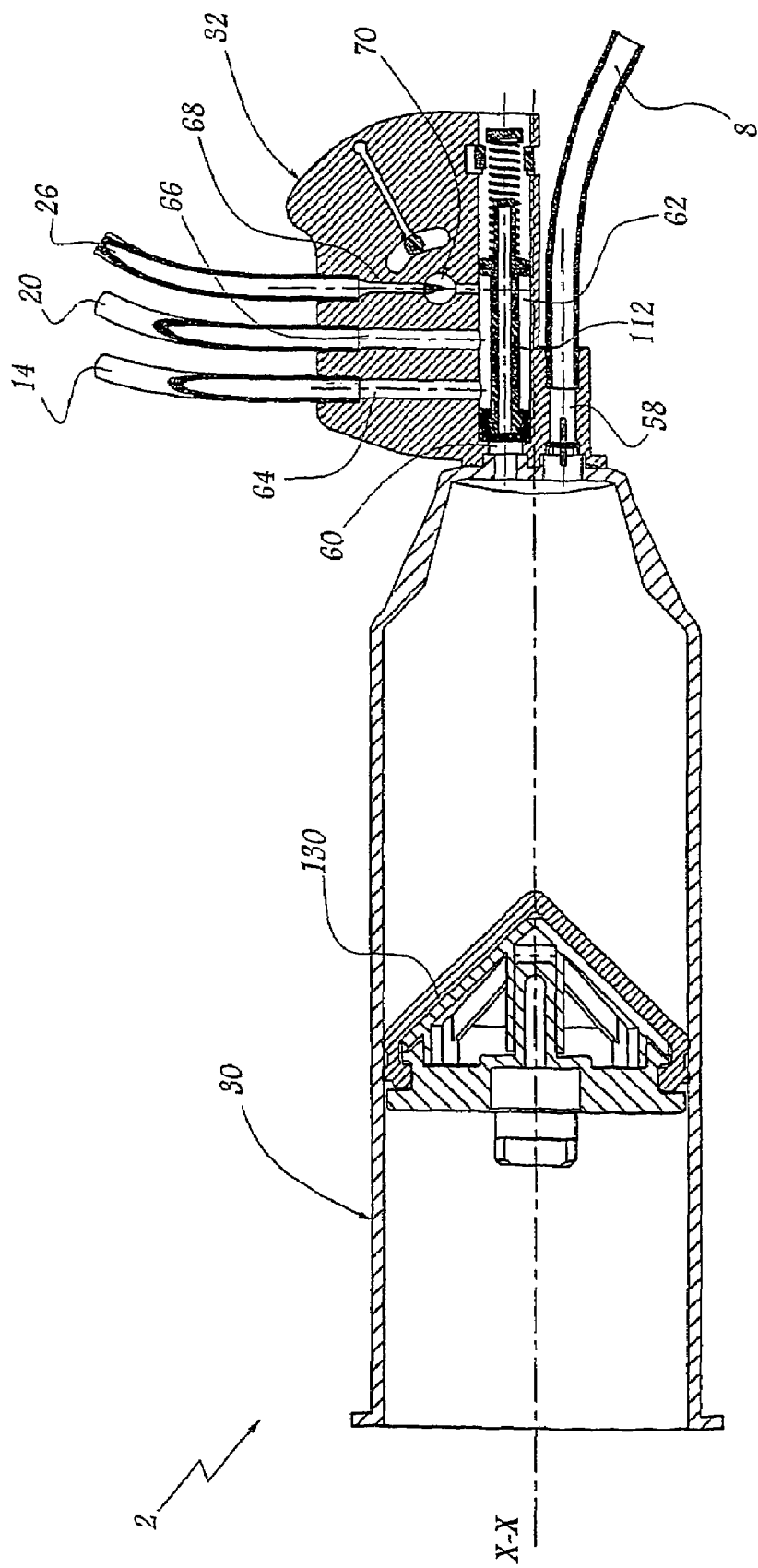
FIG. 10 is a view similar to that in FIG. 2 of a variant of the distribution device according to the invention.

FIG. 10 illustrates a variant of device 2 which is designed to incorporate the latter with a motor-driven device.

The essential difference between the device in FIG. 10 and that in the preceding figures lies in syringe body 30 and piston 40. In this variant the handles for holding syringe body 30 are absent and the piston comprises a head 130 which is designed to be fitted to a rod, not shown, which is driven by a motor, in particular by an automated system. Through such a variant contrast fluid can be injected at higher pressures than those achieved by the manual device described previously.

Various arrangements and variants of the distribution device and delivery system described hitherto may be envisaged:

distributor 32 may be made integral with the distal extremity 46 of syringe body 30 by any means which ensure the solidity and leaktight nature of such a connection, for example by adhesive bonding or by forming these parts in a single piece, in particular by moulding, unlike the embodiment illustrated, body 32A, within which tube 66 which connects the feed line for contrast fluid 4 or syringe body 30 is formed, is not necessarily formed of one piece with body 32B within which connection chamber 62 is formed, but may be mechanically independent of that body 32B, being for example either formed in one piece with the distal extremity part of the syringe body or formed of one piece with the distal extremity of the syringe body through attachment means similar to those described previously between syringe body 30 and distributor 32, deformable valve 58 may be replaced by a bead valve which is sensitive to the pressure difference obtaining on either side of the valve, and/or spring 120 returning slide 112 may be replaced by a resilient blade, for example of one piece with body 32B of distributor 32.

The invention claimed is:

1. A distribution device for a system (1) for delivery of medical fluids to a patient, comprising;

a syringe body (30), a feed tube (56) for an active medical fluid, opening into the syringe body (30) and designed to be connected to a reservoir (6) for the active medical fluid, a distributor (32) comprising a distributor body (32B), within which there is bounded a chamber (62) for fluid circulation, and within the chamber (62) there are both a slide (112), which can move in relation to the distributor body (32B) and which forms, with walls of the chamber, a compartment (126), and a resilient member (120) placed between the slide (112) and a fixed part (122) of the distributor body, an injection tube (60), for the injection of the active medical fluid, connected to a distal extremity (46) of the syringe body (30) and opening into the chamber (62), a pressurised tube (64), designed to be connected to the patient through a pressurised line (12) of the system (1), directly connected and opening into the chamber (62), a pressure measurement tube (66), designed to be connected to a pressure measurement line (16) of the system (1), and opening into the chamber (62), and a flush tube (68) which is separate from other tubes (56, 60, 64, 66) of the device, which is formed in the distributor body (32B) and which comprises a first section (68A), which is designed to be connected to a reservoir (24) for a flush medical fluid, and a second section (68B) opening directly into the chamber (62), said flush tube (68) being fitted with a valve (70, 80) equipped with a plug (70) which is located between the first and second sections (68A, 68B) of the flush tube and which can be moved manually between a position in which it at least partly closes the flush tube and a position in which the flush tube (68) is in free communication with the chamber (62), wherein the distributor provides an automatic connection via the chamber between the pressurised tube (64) and either the injection tube (60) or the pressure measurement tube (66) through the action of the pressure of the active medical fluid and the resilient member (120), the active medical fluid circulating via the compartment (126) between the pressurised tube (64) and the pressure measurement tube (66) when they are in connection, and wherein the distributor (32) connects the flush tube (68) with the pressurised tube (64) and with the pressure measurement tube (66) via the chamber (62), the flush medical fluid circulating via the compartment (126) between the flush tube (68) and the pressure measurement tube (66) when they are in connection.

2. A device according to claim 1, wherein the valve (70, 80) of the flush tube (68) is supported by the body (32B) of the distributor (32).

3. A device according to claim 1, wherein the valve (70, 80) is mounted so as to rotate about an axis (Z-Z) orientated transversely to the flush tube (68).

4. A device according to claim 1, wherein the valve in the flush tube (68) comprises a plug (70) for that tube and a manual control lever (80), the plug and the handle being both connected mechanically to each other and capable of movement with respect to the body (32B) of the distributor (32).

5. A device according to claim 4, wherein the plug (70) comprises a sector of a cylinder (74).

6. A device according to claim 1, further comprising means (94, 96) for resiliently returning the valve (70, 80) into its closed position.

7. A device according to claim 6, wherein the returning means comprises a flexible blade (94) bearing against the body (32B) of the distributor (32) and mechanically connected to the valve (70, 80) of the flush tube (68).

8. A device according to claim 1, wherein the body (32B) of the distributor (32) is made of one piece with the body of the syringe (30) in a leaktight manner.

9. A device according to claim 1, wherein the tube (56) feeding the first active medical fluid is bounded by the distributor (32).

10. A device according to claim 1, wherein the feed tube (56) and the injection tube (60) for the active medical fluid extend in substantially parallel directions.

11. A kit for the injection of a contrast product into the human body, comprising:
  a distribution device (2) according to claim 1,
  a feed line (4) for contrast product comprising a flexible conduit (8) fitted with a drip chamber (10) and designed to be connected at one extremity to a reservoir (6) for contrast fluid and at its other extremity to the feed tube (56) of the distribution device (2),
  a pressurised line (12) comprising at one extremity a coronarography catheter (15) designed to be inserted into the patient's body and designed to be connected at its other extremity the pressurised tube (64) of the distribution device (2),
  a pressure measurement line (16) incorporating a conduit (20) fitted with a pressure sensor (18) and designed to be connected to the pressure measurement tube (66) of the distribution device (2), and
  a flush line (22) comprising a flexible conduit (26) fitted with a drip chamber (28) and designed to be connected at one extremity to a reservoir (24) for a flush solution and at its other extremity to the flush tube (68) of the distribution device (2).

* * * * *